(12) United States Patent
Zhang et al.

(10) Patent No.: US 11,253,002 B2
(45) Date of Patent: Feb. 22, 2022

(54) ATOMIZER AND ELECTRONIC CIGARETTE HAVING SAME

(71) Applicant: Shenzhen First Union Technology Co., Ltd., Shenzhen (CN)

(72) Inventors: Yunkai Zhang, Shenzhen (CN); Zhengfa Li, Shenzhen (CN); Zhongli Xu, Shenzhen (CN); Yonghai Li, Shenzhen (CN)

(73) Assignee: Shenzhen First Union Technology Co., Ltd., Shenzhen (CN)

( * ) Notice: Subject to any disclaimer, the term of this patent is extended or adjusted under 35 U.S.C. 154(b) by 293 days.

(21) Appl. No.: 16/513,748

(22) Filed: Jul. 17, 2019

(65) Prior Publication Data

US 2020/0022413 A1 Jan. 23, 2020

(30) Foreign Application Priority Data

Jul. 17, 2018 (CN) .......................... 201821125199.0

(51) Int. Cl.
*A24F 47/00* (2020.01)
*A24F 40/46* (2020.01)
*A61M 11/04* (2006.01)
*A24F 40/485* (2020.01)
*A24F 40/10* (2020.01)

(52) U.S. Cl.
CPC ............ *A24F 40/46* (2020.01); *A24F 40/485* (2020.01); *A61M 11/042* (2014.02); *A24F 40/10* (2020.01); *A61M 2205/8206* (2013.01)

(58) Field of Classification Search
CPC ................ A24F 40/46; A61M 11/042; A61M 2205/8206
See application file for complete search history.

(56) References Cited

U.S. PATENT DOCUMENTS

| | | | |
|---|---|---|---|
| 8,925,555 B2 * | 1/2015 | Monsees | A61M 11/042 131/273 |
| 9,289,014 B2 * | 3/2016 | Tucker | H05B 3/0014 |
| 9,439,456 B2 * | 9/2016 | Liu | A24F 40/46 |
| 10,085,484 B2 * | 10/2018 | Li | A61M 15/06 |
| 10,716,331 B2 * | 7/2020 | Biel | A61M 15/06 |
| 2011/0303231 A1 * | 12/2011 | Li | A24F 40/46 131/329 |
| 2014/0130816 A1 | 5/2014 | Liu | |
| 2017/0188626 A1 | 7/2017 | Davis et al. | |
| 2020/0022413 A1 * | 1/2020 | Zhang | A24F 40/46 |

FOREIGN PATENT DOCUMENTS

GB 2 548 647 A 9/2017

* cited by examiner

*Primary Examiner* — Neil Abrams
(74) *Attorney, Agent, or Firm* — PROI Intellectual Property US; Klaus Michael Schmid

(57) ABSTRACT

An atomizer and an electronic cigarette having the same are disclosed. An atomizer includes an atomizing sleeve, with a reservoir formed therein; a heater, disposed inside the atomizing sleeve; as used herein, the heater includes: a quartz glass tube, hollow and with two ends open, a liquid conductive element, received in the quartz glass tube; the liquid conductive element is configured for absorbing tobacco liquid into the quartz glass tube and a heating element, sleeved on the quartz glass tube; the heating element generates infrared radiation to heat the tobacco liquid stored in the quartz glass tube.

20 Claims, 6 Drawing Sheets

ATOMIZER AND ELECTRONIC CIGARETTE HAVING SAME

TECHNICAL FIELD

The present disclosure relates to smoking articles, and particularly to an atomizer and an electronic cigarette having same.

BACKGROUND ART

The electronic cigarette is a kind of electronic product mimicking a traditional cigarette, having a same appearance, aerosol, taste and feeling with the traditional cigarette. By relying on an aerosol process, the atomizer containing nicotine would be transformed into an aerosol drawn by the user. Due to the convenience of carrying the electronic cigarette, no open flame and environmental friendly etc., the electronic cigarette is widely applied to an abundance of smokers.

The atomizer as an important component in the electronic cigarette is configured that after the atomizer is powered on, a heater in the atomizer heats the tobacco liquid stored in the atomizer to generate an aerosol drawn by the user.

The heater in the prior atomizer is generally made of metallic materials, such as a metallic heating wire or heating piece etc., the heater directly contacts with a liquid conductive element such as fiber cottons or glass fiber sleeves etc. After powered on, the heater heats the tobacco liquid temporarily stored in the liquid conductive element to generate an aerosol drawn by the user.

During the invention process, the inventors find that in a process that the above heater is heating, the heater directly contacts the fiber cottons or glass fiber sleeves while the heat generates high temperature enabling the fiber cottons or glass fiber sleeves to generate formaldehyde that is harmful to people's health in one hand; on the other hand, the heater directly contacts the tobacco liquid, the heater would get oxidized to generate some noxious substances such as metallic ions or metallic oxides etc., which are later conveyed to the tobacco liquid, these noxious substances may be absorbed by the human body along with the aerosol, therefore affecting the user's health.

SUMMARY

To overcome the above drawbacks that a heater generates noxious substances when heating, the present disclosure relates to an atomizer including a heater without generating noxious substances and an electronic cigarette having the same.

In a first aspect, an atomizer is disclosed in the present disclosure, the atomizer includes:

an atomizing sleeve, with a reservoir formed therein;
a heater, disposed inside the atomizing sleeve, the heater includes:
a quartz glass tube, hollow and with two ends opened;
a liquid conductive element, received in the quartz glass tube; the liquid conductive element is configured for absorbing tobacco liquid into the quartz glass tube;
a heating element, sleeved on the quartz glass tube; the heater generates infrared radiation to heat the tobacco liquid stored in the quartz glass tube;
Optionally, the quartz glass tube is bored with an air conductive hole extending through inside and outside walls of the quartz glass tube.

Optionally, the air conductive holes are multiple, spaced apart along an axial direction of the quartz glass tube;

Optionally, the heater includes an electronically heating wire, spirally wound around the quartz glass tube.

Optionally, the atomizer includes a first sealing element, one end of the atomizing sleeve is bored with an opening, the first sealing element is configured to seal the opening.

Optionally, the atomizer further includes an air conductive element; the air conductive element includes a body and two first retaining walls; the two first retaining walls are extending from two opposite sides of the body along a direction departing away from the opening; the two first retaining walls are dented to form two first retaining grooves.

The atomizing sleeve has a first side wall facing the opening; two second retaining walls are spaced apart and extending towards the opening; the two second retaining walls are respectively dented to form two second retaining grooves; two ends of the quartz glass tube are respectively secured by the first retaining grooves and the second retaining grooves.

Optionally, the body, the first side wall, two first retaining walls and two second retaining walls encompass an aerosolizing chamber; the heater is received in the aerosolizing chamber and the air conductive hole is received in the aerosolizing chamber.

Optionally, the air conductive element is provided with an air conductive pipe extending from the body towards the opening; an axis of the air conductive pipe is perpendicular with an axis of the quartz glass tube.

Optionally, a length of the liquid conductive element is greater than that of the quartz glass tube, two ends of the liquid conductive element are respectively exposed to outside of the quartz glass tube and disposed inside the reservoir.

In second aspect, the present disclosure relates to an electronic cigarette, including:

an atomizer, configured for heating the tobacco liquid in the atomizer to generate an aerosol; and
a power supply, configured for supplying power to the atomizer;
As used herein, the atomizer includes an aforementioned atomizer.

Compared with the prior art, in the embodiment, by relying on the hollow quartz glass tube with two ends open, the liquid conductive element is received in the quartz glass tube, the heater is sleeved on the quartz glass tube. By relying on the heater generating the infrared radiation, it may heat the tobacco liquid stored in the quartz glass tube, preventing the heater from directly contacting the liquid conductive element and the tobacco liquid with consequently generating noxious substances, which may ensure the user's health.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

Figure 1:
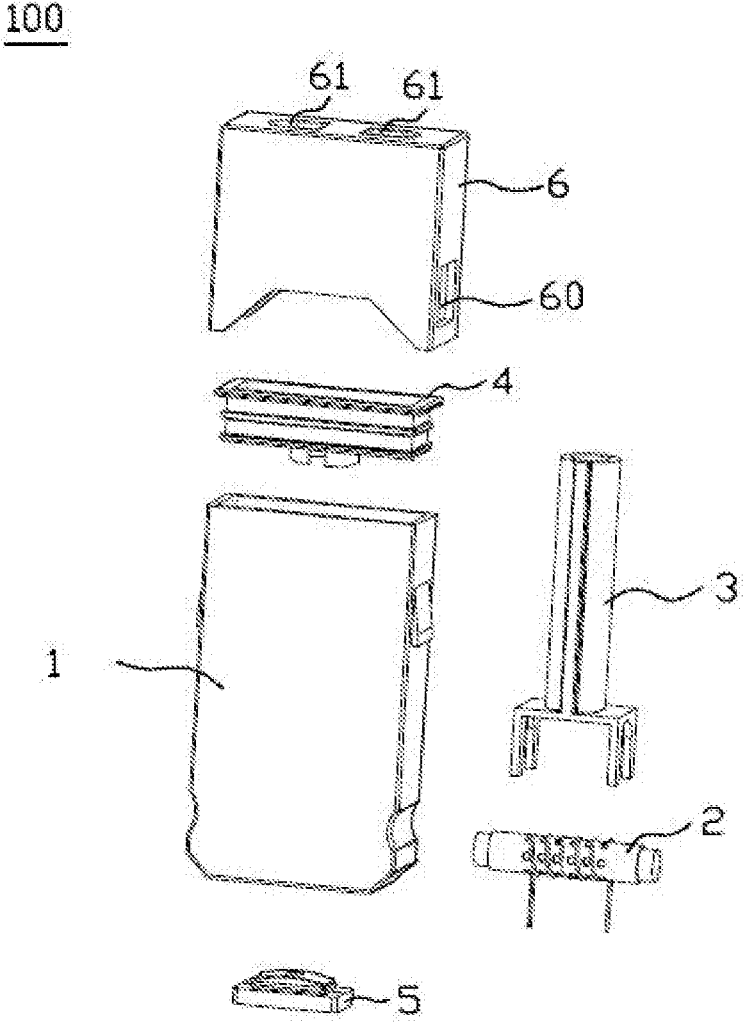
FIG. 1 is an exploded view of an atomizer according to a first embodiment of the present disclosure.

Numerals indicating components are illustrated herein:

| Atomizer 100 | Atomizing sleeve 1 | Opening 10 | First side wall 11 |
|---|---|---|---|
| First through hole 110 | Second retaining wall 111 | Second retaining groove 1110 | Second side wall 12 |
| Hook 120 | Third side wall 13 | Heater 2 | Quartz glass tube 21 |
| Air conductive hole 210 | Liquid conductive element 22 | Heating element 23 | Air conductive element 3 |
| Body 31 | First retaining wall 311 | First retaining groove 3110 | Air conductive pipe 32 |
| Air flow path 33 | First sealing element 4 | Second through hole 40 | Reservoir 41 |
| Aerosolizing chamber 30 | Second sealing element 5 | Air inlet 50 | Mouth piece 6 |
| Recess 60 | Aerosol outlet 61 | Power battery 200 | |

DETAILED DESCRIPTION

Provided herein are an electronic inhalable aerosol device (alternatively referred to as vaporization devices or electronic vaping devices etc.) generally heats a tobacco solution containing nicotine to generate an aerosol, eventually drawn by the users.

Embodiment One

The atomizer disclosed by the present disclosure typically applied to an electronic cigarette, a liquid volatilizing device or other aromatic releasing device, in this present disclosure, taking the electronic cigarette as an example.

Figure 2:
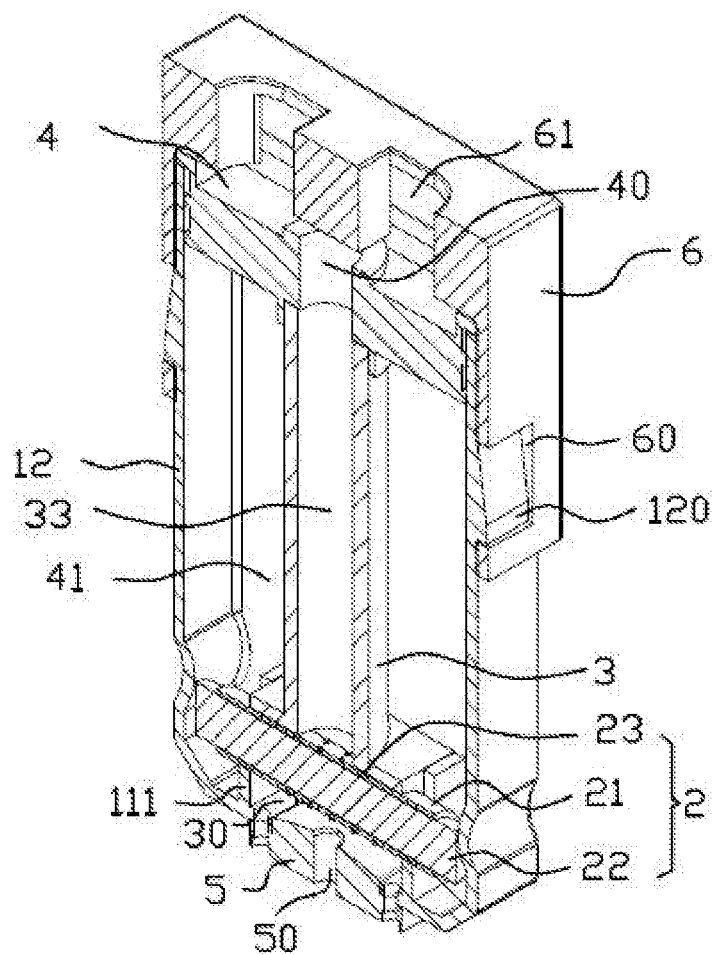
FIG. 2 is a sectional isometric view of the atomizer in FIG. 1.

Referring to FIG. 1 and FIG. 2, an atomizer 100 is provided according to an embodiment of the present disclosure. The atomizer 100 includes an atomizing sleeve 1, a heater 2, an air conductive element 3, a first sealing element 4, a second sealing element 5 and a mouthpiece 6.

Figure 3:
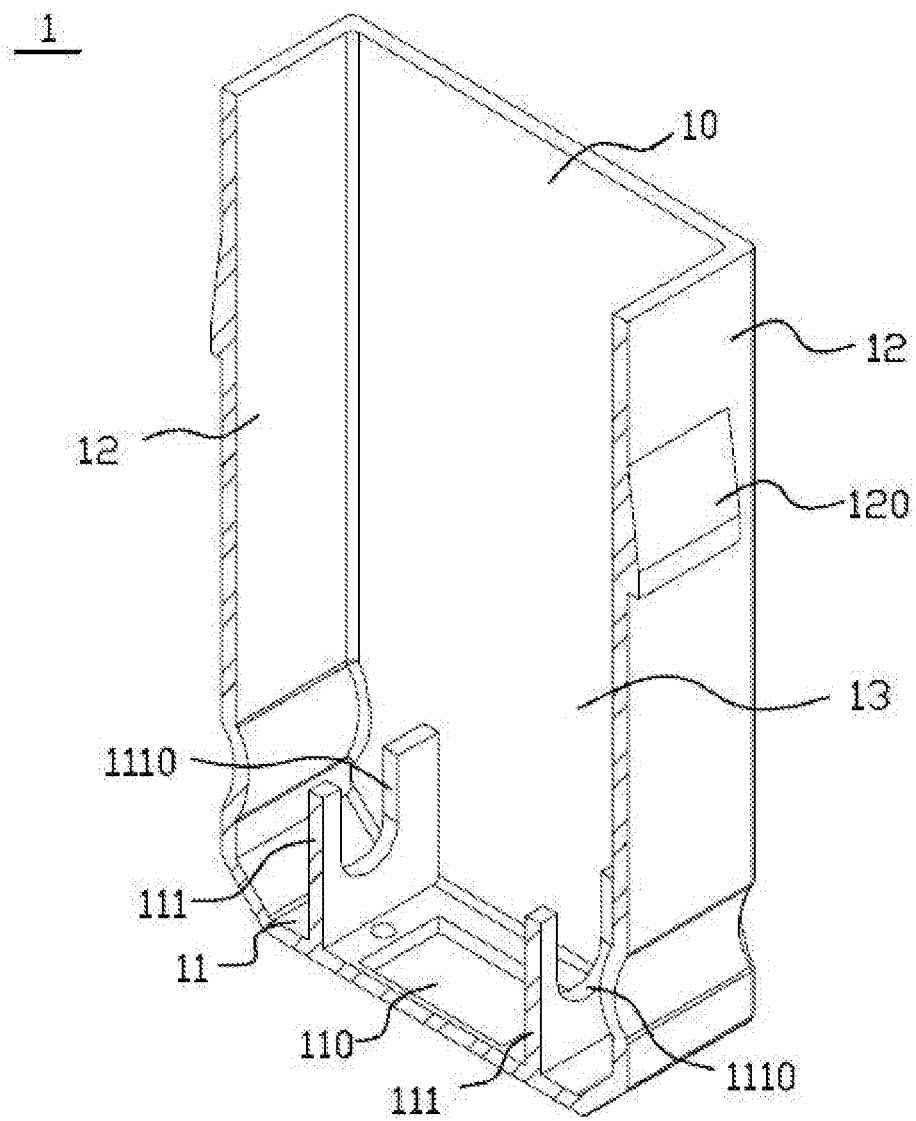
FIG. 3 is a sectional isometric view of an atomizing sleeve in the atomizer according to the first embodiment of the present disclosure.

Referring to FIG. 1 to FIG. 3, the atomizer 1 includes a first side wall 11, two second side walls 12 extending from two opposite edges of the first side wall 11, two third side walls 13 extending from the other two opposite edges of the first side wall 11. The first side wall 11, two second side walls 12 and two third side walls 13 encompass a reservoir 41 configured for storing tobacco liquid. The first side wall 11 connects one edge of the second side wall 12 and one edge of the third side wall 13, an opposite edge of the second side wall 12 and an opposite edge of the third side wall 13 forms an opening 10. The opening 10 and the first side wall 11 are respectively disposed at two opposite edges of the second side wall 12 and two opposite edges of the third side wall 13, that means the first side wall 11 and the opening 10 are oppositely set.

Two spaced-apart second retaining walls 111 are extending from the first side wall 11 towards the opening 10, in the end, the two second retaining walls 111 are dented backwards to form two second retaining grooves 1110. The first side wall 11 is bored through with a first through hole 110. The first through hole 110 is disposed between the two second retaining walls 111. A width of the second side wall 12 is less than a width of the third side wall 13 such that a cross-section of the atomizing sleeve 1 is rectangular; an outer surface of the second side wall 12 has a protruding part, e.g. a hook 120.

Two spaced-apart second retaining walls 111 are extending from the first side wall 11 towards the opening 10, in the end, the two second retaining walls 111 are dented backwards to form two second retaining grooves 1110. The first side wall 11 is bored through with a first through hole 110. The first through hole 110 is disposed between the two second retaining walls 111. A width of the second side wall 12 is less than a width of the third side wall 13 such that a cross-section of the atomizing sleeve 1 is rectangular; an outer surface of the second side wall 12 has a protruding part, e.g. a hook 120.

Figure 4:
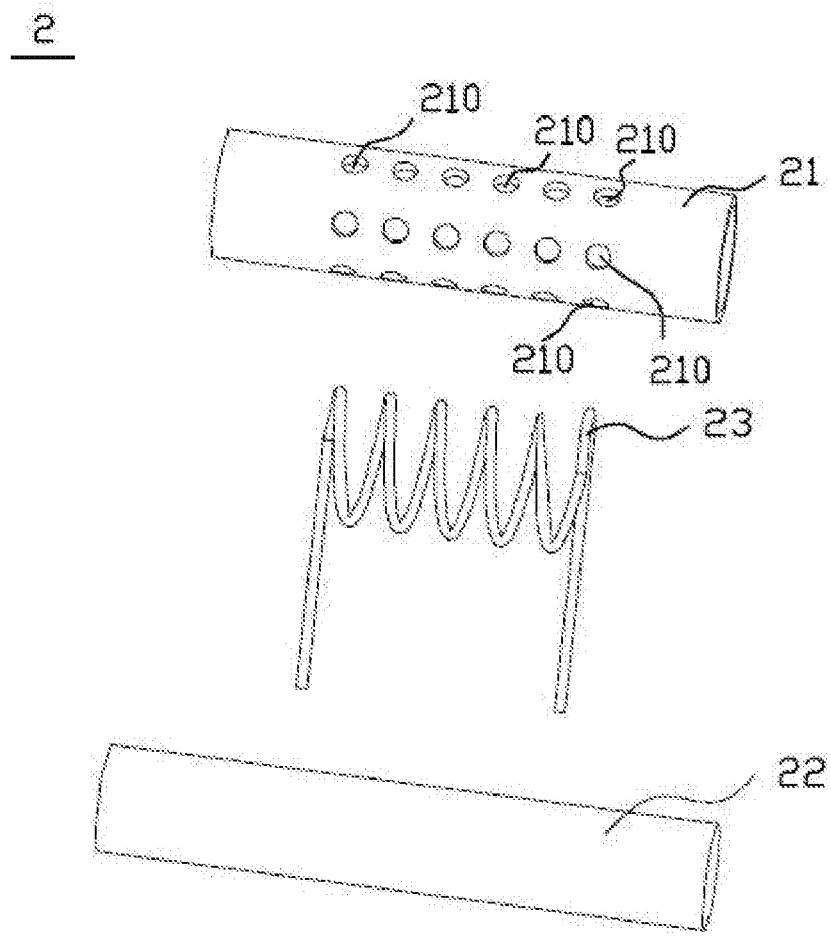
FIG. 4 is a sectional isometric view of a heater in the atomizer according to the first embodiment of the present disclosure.

Referring to FIG. 2 and FIG. 4, the heater 2 is disposed inside the atomizing sleeve 1, the heater 2 includes a quartz glass tube 21, a liquid conductive element 22 and a heating element 23.

The quartz glass tube 21 is a tubular structure with two ends opened, the quartz glass tube 21 is received in the second retaining groove 1110. The quartz glass tube 21 includes good thermostability with stable chemical properties, and doesn't generate noxious substances. Moreover, due to a special microscopic molecular structure inside the quartz glass tube 21, it may filter visible light and allow infrared radiation to penetrate into. The quartz glass tube 21 is bored with air conductive holes 210 through the inside wall and outside wall of the quartz glass tube 21, and the air conductive holes 210 are spaced apart along an axial direction of the quartz glass tube 21, the air conductive holes 210 are spaced apart along a radial direction of the quartz glass tube 21, that is the air conductive holes 210 are dispersed along an axial direction of the quartz glass tube 21 in linear array and the air conductive holes 210 are dispersed along an radial direction of the quartz glass tube 21 in circumferential array.

The liquid conductive element 22 is cylindrical, the liquid conductive element 22 is received and secured inside the quartz glass tube 21, a length of the liquid conductive element 22 is longer than the length of the quartz glass tube 21; two ends of the liquid conductive element 22 are exposed to outside the quartz glass tube 21 but inside the reservoir 41. The liquid conductive element 22 is configured for conveying the tobacco liquid from reservoir 41 to inside the quartz glass tube 21, especially via two ends of liquid conductive element 22.

The liquid conductive element 22 includes at least one or more selected from fiber cottons, glass fiber sleeves, microporous ceramics and cellular metallic materials etc.

The heater 23 includes metallic alloys, such as nickelchrome etc. In some embodiments, the heater 23 is a electrically heating wire, wound around the quartz glass tube 21. After powered on, the heater 23 generates heat radiation and infrared radiation into the quartz glass tube 21 for heating the tobacco liquid stored in the liquid conductive element 22 such that the tobacco liquid is vaporized as an aerosol. On one hand, the heater 23 doesn't contact with the liquid conductive element 22 and tobacco liquid stored therein, without generating noxious substances due to the direct contacting of the heater 23 with the liquid conductive element 22 and the tobacco liquid therein, which may ensure the user's health. On the other hand, the heater 23 simultaneously generates the heat radiation and infrared radiation into the quartz glass tube 21, therefore the heating efficiency is more even compared with the metallic heating wire.

Figure 5:
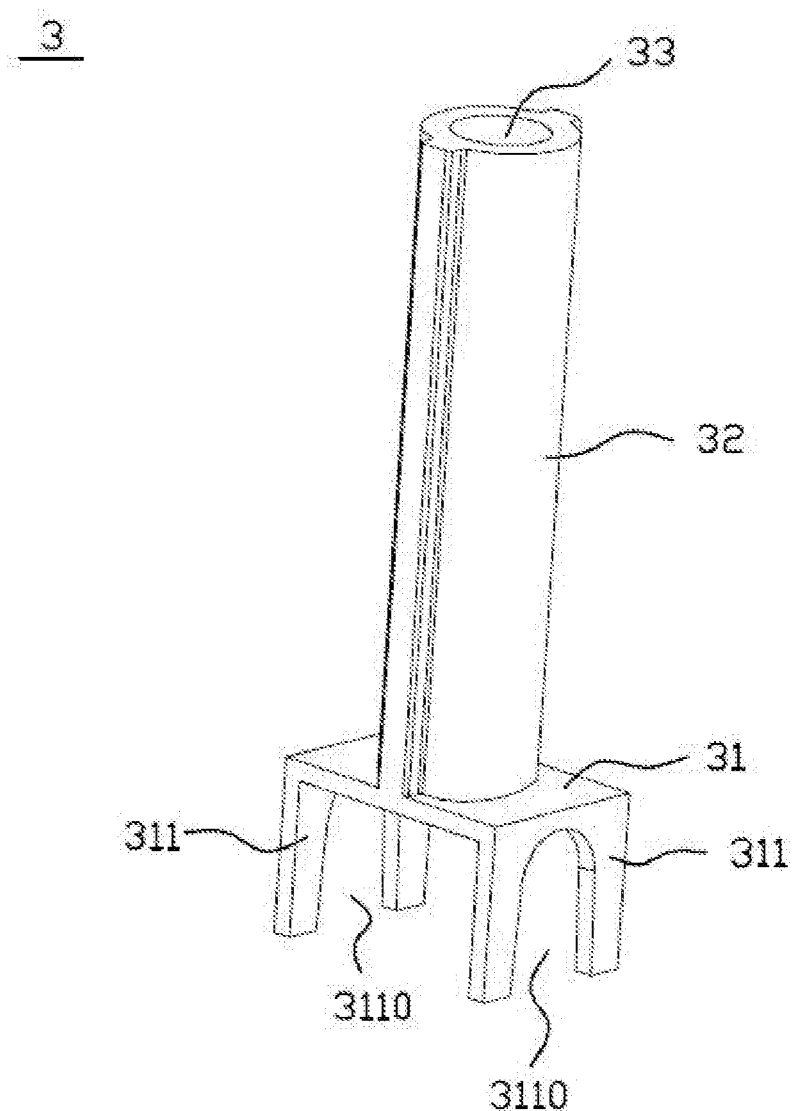
FIG. 5 is an exploded view of an air conductive element in the atomizer according to the first embodiment of the present disclosure.

Referring to FIG. 2 and FIG. 5, the air conductive element 3 includes a body 31, two first retaining walls 311 and an air conductive pipe 32.

The body 31 is plate-shaped, the two first retaining walls 311 are extending from two opposite edges of the body 31 towards the opening 10, that is two first retaining walls 311 are extending from two opposite edges of the body 31 towards the first side wall 11. An end face of the first retaining walls 311 is dented towards the aerosol outlet 61 to form a first retaining groove 3110; two ends of the quartz glass tube 21 are respectively received in the first retaining groove 3110, that is securing the quartz glass tube 21 by the first retaining groove 3110 and the second retaining groove 1110 clamped with each other. The two first retaining walls 311 are disposed between two second retaining walls 111 such that the first retaining walls abutting against the two first side walls 11. The body 31, the first side walls 11, the two first retaining walls 311 and the two second retaining walls 111 encompass an atomizing chamber 30. The heater 23 is received in the atomizing chamber 30, the air conductive hole 210 is received in the atomizing chamber 30.

The air conductive pipe 32 is extending from a middle of the body 31 towards the opening 10. An axial direction of the air conductive pipe 32 is perpendicular to the axial direction of the quartz glass tube 21, that is the air conductive pipe 32 is arranged vertically while the quartz glass tube 21 is arranged transversely. The air conductive element 3 is provided with an air flow path 33 through the air conductive pipe 32 and the body 31, the air flow path 33 is in communication with the atomizing chamber 30.

Referring to FIG. 1 and FIG. 2, the first sealing element 4 includes silica gel. A middle of the first sealing element 4 is provided with a second through hole 40 through the first sealing element 4. The second through hole 40 is in communication with the air flow path 33. The first sealing element 4 is configured for sealing the opening 10. The first sealing element 4, the air conductive element 3 and the atomizing sleeve 1 encompass the reservoir 41. The reservoir 41 is separated from the atomizing chamber 30. The tobacco liquid in the reservoir 41 is conveyed to the quartz glass tube 21 via the liquid conductive element 22. By relying on heat radiation and infrared radiation of the heater 23, an aerosol is generated to flow into the atomizing chamber 30.

Understandable, intersection of the first retaining wall 311, the second retaining wall 111 and the quartz glass tube 21 is sealed by silicone materials to prevent the tobacco liquid in reservoir 41 from flowing into the atomizing chamber 30 without being heated by the heater 2.

Referring to FIG. 1 and FIG. 2, the second sealing element 5 is configured for sealing the through holes of the first side wall 11. The second sealing element 5 is bored with an air inlet 50 through the second sealing element 5. The air inlet 50 is in communication with the atomizing chamber 30.

Referring to FIG. 1 and FIG. 2, the mouthpiece 6 is sleeved on the atomizing sleeve 1, a side wall of the mouthpiece 6 abutting the second side wall 12 is bored with a recess 60 that is matched with the hook 120, which realizes the snap joint between the mouthpiece 6 and the atomizing sleeve 1. A side wall of the mouthpiece 6 abutting the first side wall 11 is bored with an aerosol outlet 61. The aerosol outlet 61 is in communication with the air flow path 33.

When assembling the atomizer 100, firstly, the liquid conductive element 22 is received and secured in the quartz glass tube 21; then the heating element 23 is sleeved on the quartz glass tube 21 to finish the assembling of the heater 2, then the heater 2 is disposed inside the second retaining groove 1110, afterwards, clamping the air conductive element 3 with two ends of the quartz glass tube 21, and sealing interjection of the first retaining wall 311, the second retaining wall 111 and the quartz glass tube 21, then injecting tobacco liquid into the reservoir 41, then putting the first sealing element 4 on the opening 10 and putting the second sealing element 5 on the first side wall 11; eventually, the mouthpiece 6 is sleeved on the atomizing sleeve 1 to finish the assembly of the atomizer 100.

Understandable, the steps for assembling the atomizer 100 is not sole and may be adjusted in accordance with the situation.

After the atomizer 100 is powered on, that is the heating element 23 is powered on, the heating element 23 generates the heat radiation and infrared radiation to the quartz glass tube 21 and the tobacco liquid in the liquid conductive element 22 is heated to generate an aerosol, the aerosol is expelled from the air conductive holes 210 on the quartz glass tube 21 into the atomizing chamber 30. When the user draws the electronic cigarette, external air flows into the atomizing chamber 30 via the air conductive holes 210, carrying the aerosol to be drawn into the user's mouth via the aerosol outlet 61 of the mouthpiece 6, through the air flow path 33.

In the embodiments, by replying on the hollow quartz glass tube 21 with two ends opened, the liquid conductive element 21 is received in the quartz glass tube 21 and the heating element 23 is sleeved on the quartz glass tube 21. By replying on the heating element 23 generating heat radiation and infrared radiation, the tobacco liquid in the quartz glass tube 21 is heated, which may prevent the heating element 23 from directly contacting the liquid conductive element 22 and the tobacco liquid to generate noxious substances, ensuring the user's health on one hand, on the other hand, compared to the metallic heating element, the heating element 23 simultaneously generates heat radiation and infrared radiation to the quartz glass tube 21, therefore the heating process is more even.

Embodiment Two

Figure 6:
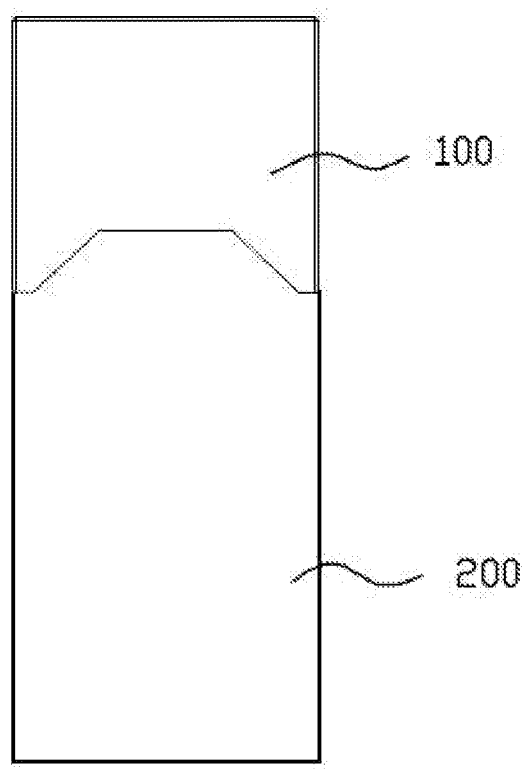
FIG. 6 is an aspect view of the electronic cigarette according to a second embodiment of the present disclosure.

Referring to FIG. 6, which is an aspect view of the electronic cigarette according to a second embodiment of the present disclosure. The electronic cigarette includes an atomizer 100 and a power supply set 200. The power supply set 200 is configured for supplying power to the atomizer 100. As used herein, the atomizer 100 is the same as the aforementioned atomizer in the embodiment one, which is no further description herein.

As used herein, the power supply set 200 includes a battery (not shown), the battery includes one or more of a dry battery, a lithium battery and a rechargeable battery etc.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer comprising:
an atomizing sleeve, with a reservoir formed therein;
a heater, disposed inside the atomizing sleeve, the heater comprising:
 a quartz glass tube, hollow and with two ends opened;
 a liquid conductive element, received in the quartz glass tube; the liquid conductive element is configured for absorbing tobacco liquid into the quartz glass tube;

a heating element, sleeved on the quartz glass tube; the heating element generates infrared radiation to heat the tobacco liquid stored in the quartz glass tube.

2. The atomizer according to claim 1, wherein the quartz glass tube is bored with an air conductive hole extending through inside and outside wall of the quartz glass tube.

3. The atomizer according to claim 2, wherein the air conductive holes comprise multiple, spaced apart along an axial direction of the quartz glass tube.

4. The atomizer according to claim 2, wherein the air conductive holes comprises multiple, spaced apart along a radial direction of the quartz glass tube.

5. The atomizer according to claim 2, wherein the heater comprises an electronically heating wire, spirally wound around the quartz glass tube.

6. The atomizer according to claim 5, wherein the atomizer comprises a first sealing element; one end of the atomizing sleeve is bored with an opening; the first sealing element is configured to seal the opening.

7. The atomizer according to claim 6, wherein the atomizer comprises an air conductive element; the air conductive element comprises a body and two first retaining walls; the two first retaining walls are extending from two opposite sides of the body along a direction departing away from the opening; the two first retaining walls are dented to form two first retaining grooves;
the atomizing sleeve comprises a first side wall facing the opening; two second retaining walls are spaced apart and extending towards the opening; the two second retaining walls are respectively dented to form two second retaining grooves; two ends of the quartz glass tube are respectively clamped by the first retaining grooves and the second retaining grooves.

8. The atomizer according to claim 7, wherein the body, the first side wall, two first retaining walls and two second retaining walls encompass an aerosolizing chamber; the heating element is received in the aerosolizing chamber and the air conductive hole is received in the aerosolizing chamber.

9. The atomizer according to claim 8, wherein the air conductive element is provided with an air conductive pipe extending from the body towards the opening; an axis of the air conductive pipe is perpendicular with an axis of the quartz glass tube.

10. The atomizer according to claim 8, wherein a length of the liquid conductive element is greater than that of the quartz glass tube, two ends of the liquid conductive element are respectively exposed to outside of the quartz glass tube and inside the reservoir.

11. An electronic cigarette comprising:
an atomizer, configured for heating the tobacco liquid in the atomizer to generate an aerosol; and
a power supply, configured for supplying power to the atomizer;
wherein the atomizer comprising:
an atomizing sleeve, with a reservoir formed therein;
a heater, disposed inside the atomizing sleeve, the heater comprising:
a quartz glass tube, hollow and with two ends opened;
a liquid conductive element, received in the quartz glass tube; the liquid conductive element is configured for absorbing tobacco liquid into the quartz glass tube;
a heating element, sleeved on the quartz glass tube; the heating element generates infrared radiation to heat the tobacco liquid stored in the quartz glass tube.

12. The electronic cigarette according to claim 11, wherein the quartz glass tube is bored with an air conductive hole extending through inside and outside wall of the quartz glass tube.

13. The electronic cigarette according to claim 12, wherein the air conductive holes comprise multiple, spaced apart along an axial direction of the quartz glass tube.

14. The electronic cigarette according to claim 12, wherein the air conductive holes comprises multiple, spaced apart along a radial direction of the quartz glass tube.

15. The electronic cigarette according to claim 12, wherein the heater comprises an electronically heating wire, spirally wound around the quartz glass tube.

16. The electronic cigarette according to claim 15, wherein the atomizer comprises a first sealing element; one end of the atomizing sleeve is bored with an opening; the first sealing element is configured to seal the opening.

17. The electronic cigarette according to claim 16, wherein the atomizer comprises an air conductive element; the air conductive element comprises a body and two first retaining walls; the two first retaining walls are extending from two opposite sides of the body along a direction departing away from the opening; the two first retaining walls are dented to form two first retaining grooves;
the atomizing sleeve comprises a first side wall facing the opening; two second retaining walls are spaced apart and extending towards the opening; the two second retaining walls are respectively dented to form two second retaining grooves; two ends of the quartz glass tube are respectively clamped by the first retaining grooves and the second retaining grooves.

18. The electronic cigarette according to claim 17, wherein the body, the first side wall, two first retaining walls and two second retaining walls encompass an aerosolizing chamber; the heating element is received in the aerosolizing chamber and the air conductive hole is received in the aerosolizing chamber.

19. The electronic cigarette according to claim 18, wherein the air conductive element is provided with an air conductive pipe extending from the body towards the opening; an axis of the air conductive pipe is perpendicular with an axis of the quartz glass tube.

20. The electronic cigarette according to claim 18, wherein a length of the liquid conductive element is greater than that of the quartz glass tube, two ends of the liquid conductive element are respectively exposed to outside of the quartz glass tube and inside the reservoir.

* * * * *